United States Patent [19]

Shroot et al.

[11] Patent Number: 4,892,864
[45] Date of Patent: Jan. 9, 1990

[54] PHARMACEUTICAL AND COSMETIC COMPOSITIONS CONTAINING AS AN ACTIVE COMPONENT 10-ACETYL-1,8,9-TRIACETOXY ANTHRACENE

[75] Inventors: Braham Shroot, Antibes; Gérard Lang, Epinay-sur-Seine; Jean Maignan, Tremblay les Gonesse, all of France

[73] Assignee: Centre International de Recherches Dermatologiques (C.I.R.D.), Valbonne, France

[21] Appl. No.: 153,600

[22] Filed: Feb. 8, 1988

Related U.S. Application Data

[63] Continuation of Ser. No. 58,324, Jun. 4, 1987, abandoned, which is a continuation of Ser. No. 756,300, Jul. 18, 1985, abandoned.

[30] Foreign Application Priority Data

Jul. 19, 1984 [FR] France .................. 84 11441

[51] Int. Cl.$^4$ ............... A61K 31/21; A61K 7/06
[52] U.S. Cl. ..................... 514/510; 424/70
[58] Field of Search ............ 514/510; 424/70

[56] References Cited

PUBLICATIONS

Chemical Abstracts 81:77722s, (1974).

*Primary Examiner*—Jerome D. Goldberg
*Attorney, Agent, or Firm*—Cushman, Darby & Cushman

[57] ABSTRACT

Pharmaceutical and cosmetic compositions contain as the active component 10-acetyl-1,8,9-triacetoxy anthracene.

6 Claims, No Drawings

PHARMACEUTICAL AND COSMETIC COMPOSITIONS CONTAINING AS AN ACTIVE COMPONENT 10-ACETYL-1,8,9-TRIACETOXY ANTHRACENE

This is a continuation of application Ser. No. 58,2324 filed June 4, 1987 now abandoned which is a continuation of Ser. No. 756,300 filed July 18, 1985, now abandoned.

The present invention relates to new pharmaceutical and cosmetic compositions, particularly anti-inflammatory compositions, containing as the active component 10-acetyl-1,8,9-triacetoxy anthracene.

10-acetyl-1,8,9-triacetoxy anthracene has been prepared and described by O.E. Schultz and H. Schultz-Mosgau, Archiv der Pharmazie, 298 313-320 (1965).

10-acetyl-1,8,9-triacetoxy anthracene has the formula

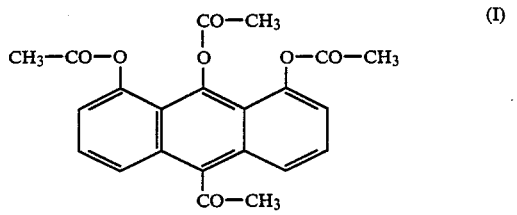

It is provided in the form of a crystallized solid having a melting point of 206° C.

It has now been discovered that this component possesses anti-inflammatory properties. It can be used in cosmetology principally for body and hair hygiene or in therapeutics or in dermo-pharmacy, particularly to inhibit abnormal proliferation of cells observed in disorders such as psoriasis, or warts, and also as an anti-inflammatory agent in the treatment of rheumatism, dermatosis, eczema, seborrheic and pellicular poll evil, and sunburns.

The present invention also relates to new pharmaceutical or cosmetic compositions characterized the the fact that they contain, as the active component, 10-acetyl-1,8,9-triacetoxy anthracene.

These compositions contain the active component in combination with an appropriate vehicle for administration, enterally, topically or parenterally. In these compositions, the concentration of the active component generally ranges from 0.01 to 70 percent by weight, generally as a function of the form of administration or application selected.

Compositions administered enterally or parenterally can be provided in the form of tablets, granules, gelules, capsules, syrups, drinkable suspensions, packeted ingestible powders, or even in the form of injectable solutions or suspensions.

For topical application, the compositions of the present invention can be provided in the form of ointments, unguents, creams, gels, sprays, suspensions, micronized powders, tinctures, solutions, lotions or shampoos.

These compositions can also contain inert adjuvants, for example, binders, fillers, diluents, thickening agents, preservatives, UVA and UVB filters, anti-oxidants and the like, or even biologically active additives.

The compositions administered orally can also contain sapidity agents.

These pharmaceutical compositions are prepared in accordance with conventional procedures.

The posology varies particularly as a function of the disorder being treated and the method of administration selected. For enteral or parenteral administration, generally from 0.005 to 5 g of the active component are administered daily to an adult, in one or several doses.

For topical application, 1 to 5 g, for example of a formulation containing from 0.01 to 5 g of the active component per 100 g of the composition are applied.

Because of the anti-inflammatory properties of the compound of formula I, the compositions of the present invention can be employed particularly in the treatment of eczema, psoriasis, rheumatism, dermatosis, warts, seborrheic and pellicular poll evil and sunburns.

The present invention also relates to a medicine packaged and prepared industrially, characterized by the fact that it comprises a pharmaceutical composition such as defined above, in an appropriate container provided with a label indentifying the method of administration recommended for the treatment of inflammatory disorders.

The present invention also relates to the use of the compound of formula I (also referred to herein as compound I) in the industrial preparation of a packaged medicine such as defined above.

The following non-limiting examples illustrate the present invention.

EXAMPLE 1

Effervescent tablet weighing 0.5 g

| | |
|---|---|
| 10-acetyl-1,8,9-triacetoxy anthracene | 0.100 g |
| Sodium bicarbonate | 0.022 g |
| Citric acid (granules) | 0.167 g |
| Powdered gum arabic | 0.005 g |
| Stearic acid | 0.002 g |
| Mucilage of gum arabic, 20%, sufficient amount | |
| Powdered flavoring, sufficient amount | |
| Finely pulverized sucrose, sufficient amount for | 0.500 g |

EXAMPLE 2

Gelule weighing 0.46 g (a) Formual for the powder

| (a) Formual for the powder | |
|---|---|
| 10-acetyl-1,8,9-triacetoxy anthracene | 0.30 g |
| Corn starch | 0.06 g |
| Magnesium stearate | 0.01 g |
| Sucrose, sufficient amount for | 0.46 g |

(b) The above powder is packaged in a gelule made of gelatin and $TiO_2$.

EXAMPLE 3

Drinkable suspension

| | |
|---|---|
| 10-acetyl-1,8,9-triacetoxy anthracene | 16.667 g |
| Glycerine | 33.333 g |
| Sucrose | 8.333 g |
| Polyoxyethylene glycol 400 | 8.333 g |
| Purified water, sufficient amount for | 100.000 g |

This suspension is packaged in a brown glass flask. It must be vigorously stirred before use.

EXAMPLE 4

Oily suspension, injectable intramuscularly

| | |
|---|---|
| 10-acetyl-1,8,9-triacetoxy anthracene | 0.004 g |
| Peanut oil, sufficient amount for | 0.750 ml |

EXAMPLE 5

Composition for topical application (A) Anhydrous hydrophobic gel

| | |
|---|---|
| Compound I | 1.00 g |
| Aerosil 200, silica, sold by Degussa | 7.00 g |
| Isopropyl myristate, sufficient amount for | 100.00 g |

(B) Occlusive hydrophobic ointment

| | |
|---|---|
| Compound I | 1.60 g |
| Ceresin | 15.00 g |
| Petrolatum oil | 35.00 g |
| Petrolatum, sufficient amount for | 100.00 g |

(C) Transparent fluid hydrophobic gel

| | |
|---|---|
| Compound I | 0.10 g |
| Rhodorsil 47 V 300, silicone oil (dimethyl polysiloxane) sold by Rhone Poulenc | 70.00 g |
| Abil 300.00 cst, silicone oil (dimethyl polysiloxane) sold by Goldschmidt, sufficient amount for | 100.00 g |

(D) Hydrophobic ointment in the form of a paste

| | |
|---|---|
| Compound I | 1.50 g |
| Isopropyl myristate | 36.40 g |
| Rhodorsil 47 V 300 | 36.40 g |
| Beeswax | 13.60 g |
| Abil 300.00 cst, sufficient amount for | 100.00 g |

(E) Single dose shampoo in 2 parts to be admixed at time of use.

| | |
|---|---|
| (i) Treating part in the form of a suspension | |
| Compound I | 0.50 g |
| Petrolatum oil, sufficient amount for | 100.00 g |
| (ii) Washing part | |
| Compound A (dodecanediol polyglycidolated with 3.5 moles of glycidol, produced by Chimex) | 20.00 g |
| Compound B, having the formula HO—(CHR—CH$_2$—O)$_x$—(CH$_2$—CH$_2$—O)$_n$—(CH$_2$—CHR—O)$_y$—H wherein R is —C$_{14}$H$_{29}$, n = about 70 and x + y = 3, produced by Chimex | 1.75 g |
| Water, sufficient amount for | 100.00 g |

The treating part must be vigorously stirred before being admixed in an applicator flask with the washing part in a ratio of 10/90. The resulting mixture must be used immediately.

EXAMPLE 6

Antitumoral activity study on lymphocytic leukemia P 388

The principle of the test is the following:
There is implanted in a mouse, at day 0, a tumor by intraperitoneal injection of 10$^6$ tumoral cells in 0.1 ml of ascitic, diluted fluid. The tumoral cells were leukemia lymphocytes (strain P 388). The treatment consists in administering intraperitoneally and daily the product studied, for 5 days following the implantation of the tumor, at various dosages.

The results of the test are set forth in Table I.

TABLE I

| Posology mg/kg | Activity | | |
|---|---|---|---|
| | Median time of survival (in days) | | $\frac{T}{C} \times 100$ |
| | Animals tested, T | Animals control, C | |
| 3.12 | 12.3 | 9.9 | 124 |
| 1.56 | 11.8 | 9.9 | 119 |
| 0.79 | 11.4 | 9.9 | 115 |

A product is considered active in this test when: $T/C \times 100 > 120$.

This study shows that the compound of formula I is active at a dosage near 3 mg/kg.

EXAMPLE 7

Study of the antitumoral activity on melanocarcinoma B 16

The principle of the test is as follows:

A mouse is implanted at day 0, with a tumor by injecting it intraperitoneally with 0.5 ml of a diluted (1/10) homogeneate of the selected tumor. The treatment consists in administering the product studied, daily and intraperitoneally, for 9 days following the implantation of the tumor.

A product is considered active, according to this test, when the ratio $T/C \times 100 > 125$.

It has been found that the optimum dose of 10-acetyl1,8,9-triacetoxy anthracene is near 6 mg/kg (for 6 mg/kg, $T/C \times 100 = 150$)

EXAMPLE 8

Study of the anti-inflammatory activity

The method used is that described by M. J. H. Smith and J. R. Walker in the British Journal of Pharmacology (198), 69, 473-478.

This method constitutes a test of chemokinese of the polymorphonuclears (category of white corpuscles) of rabbit. The chemokinese is stimulated by a chemotactic agent (fMLP* 1mM). The inhibition, caused by the product being studied at increasing dosages, is studied. There is then determined the $K_{0.5}$ value (in micromoles/liter) which corresponds to a 50% reduction of the maximum stimulation given by only fMLB 1mM.

* fMLP is formylmethionyl leucylphenylalanine.

With compound I: $K_{0.5} = 36$ micromoles/liter.

EXAMPLE 9

Study of the antiproliferative activity on fibroblasts

The method used is that described by Jacques and Reichert in the British Journal of Dermatology 105, Supplement 20, pp. 45–48 (1981).

This method consists in evaluating the cytostatic activity of the product on fibroblasts by studying the inhibition of the incorporation of tritiated thymidine in a culture of fibroblasts of human skin.

The product studied is added at various increasing concentrations. The dose $K_{0.5}$ is determined which is the dose, expressed in micromoles/liter, necessary for a 50% reduction, relative to non-treated cultures, of the incorporation of tritiated thymidine.

With compound I, it has been found that $K0.5 = 1$ micromole/liter.

What is claimed is:

1. A pharmaceutical composition for the treatment of eczema, rheumatism, dermatosis, seborrhea, pellicular poll evil, sunburn, psoriasis or warts comprising in a pharmaceutically acceptable carrier from 0.01 to 70 percent by weight, based on the total weight of said composition of 10-acetyl-1,8,9-triacetoxy anthracene as the active component, said composition being in the form of tablets, granules, gelules and capsules.

2. A cosmetic composition for body and hair hygiene comprising in a cosmetically acceptable carrier from 0.01 to 70 percent by weight, based on the total weight of said composition, of 10-acetyl-1,8,9-triacetoxy anthracene as the active component, said composition being in the form of a cream, gel, spray or shampoo.

3. A method for the treatment of eczema, rheumatism, dermatosis, seborrhea, pelllicular poll evil, sunburn, psoriasis or warts comprising administering to an adult suffering from eczema, rheumatism, dermatosis, seborrhea, pellicular poll evil, sunburn, psoriasis, or warts in an amount effective for the treatment of said eczema, rheumatism, dermatosis, seborrhea, poll evil, sunburn, psoriasis or warts, pharmaceutical composition comprising in a pharmaceutically acceptable carrier from 0.01 to 70 percent by weight, based on the total weight of said pharmaceutical composition, of 10-acetyl-1,8,9-triacetoxy anthracene as the active component.

4. The method of claim 3 wherein said carrier is one for enteral or parenteral administration, said active component being administered at a daily rate of from 0.005 to 5 g.

5. The method of claim 3 wherein said carrier is one suitable for topical administration, said active component being present in said composition in an amount ranging from 1 to 5 g per 100 g of said composition.

6. A method for body and hair hygiene comprising topically administering to said body or hair, in an amount effective for said body and hair hygiene, a cosmetic composition comprising in a cosmetically acceptable carrier form 0.01 to 70 percent by weight, based on the total weight of said cosmetic composition, of 10-acetyl-1,8,9-triacetoxy anthracene as the active component.

* * * * *